United States Patent
Zhigaltsev et al.

(10) Patent No.: US 7,273,620 B1
(45) Date of Patent: Sep. 25, 2007

(54) TRIGGERED RELEASE OF LIPOSOMAL DRUGS FOLLOWING MIXING OF CATIONIC AND ANIONIC LIPOSOMES

(75) Inventors: Igor V. Zhigaltsev, Vancouver (CA); Kim F. Wong, Vancouver (CA); Norbert Maurer, Vancouver (CA); Pieter R. Cullis, Vancouver (CA)

(73) Assignee: University of British Columbia, Vancouver (CA)

( * ) Notice: Subject to any disclaimer, the term of this patent is extended or adjusted under 35 U.S.C. 154(b) by 653 days.

(21) Appl. No.: 10/441,781

(22) Filed: May 19, 2003

Related U.S. Application Data (60) Provisional application No. 60/382,183, filed on May 20, 2002.

(51) Int. Cl.
*A61K 9/127* (2006.01)
(52) U.S. Cl. .................................................. 424/450
(58) Field of Classification Search .................. None
See application file for complete search history.

(56) References Cited

U.S. PATENT DOCUMENTS

| | | | |
|---|---|---|---|
| 4,186,183 A | 1/1980 | Steck et al. ................... 424/38 |
| 4,217,344 A | 8/1980 | Vanlerberghe et al. ......... 424/60 |
| 4,235,871 A | 11/1980 | Papahadjopoulos et al. .. 424/19 |
| 4,261,975 A | 4/1981 | Fullerton et al. ............. 424/89 |
| 4,485,054 A | 11/1984 | Mezei et al. .................. 264/4.6 |
| 4,501,728 A | 2/1985 | Geho et al. .................... 424/38 |
| 4,603,044 A | 7/1986 | Geho et al. ..................... 424/9 |
| 4,737,323 A | 4/1988 | Martin et al. ................. 264/4.3 |
| 4,774,085 A | 9/1988 | Fidler ......................... 424/85.5 |
| 4,837,028 A | 6/1989 | Allen .......................... 424/450 |
| 4,885,172 A | 12/1989 | Bally et al. .................. 424/417 |
| 4,897,355 A | 1/1990 | Eppstein et al. .......... 435/240.2 |
| 4,946,787 A | 8/1990 | Eppstein et al. .......... 435/240.2 |
| 4,957,773 A | 9/1990 | Spencer et al. ................ 427/39 |
| 5,023,087 A * | 6/1991 | Yau-Young .................. 424/450 |
| 5,059,421 A | 10/1991 | Lougrey et al. ............. 424/417 |
| 5,077,056 A | 12/1991 | Bally et al. .................. 424/450 |
| 5,171,578 A | 12/1992 | Bally et al. .................. 424/450 |
| 5,208,036 A | 5/1993 | Eppstein et al. ............. 424/450 |
| 5,279,833 A | 1/1994 | Rose ........................... 424/450 |
| 5,532,152 A | 7/1996 | Cousens et al. ............. 435/197 |

(Continued)

FOREIGN PATENT DOCUMENTS

WO    WO91/17424    11/1991

OTHER PUBLICATIONS

Bailey, A. et al., "Membrane Fusion with Cationic Liposomes: Effects of Target Membrane Lipid Composition," *Biochemistry* 36(7):1628-1634, Feb. 1997.

(Continued)

*Primary Examiner*—Gollamudi S. Kishore
(74) *Attorney, Agent, or Firm*—Seed IP Law Group PLLC (57) ABSTRACT

Methods and compositions for triggering the delivery of an encapsulated therapeutic agent from a liposome are provided. Liposomes of opposite charge and incorporating lipids which favor non-lamellar structures are contacted in vivo. At least one of the liposome encapsulates at least one therapeutic drug or agent. Preferably, the liposomes have a fusogenic hydrophillic coating, such as PEG to control the rate of interaction of the liposomes and release of the therapeutic agent.

14 Claims, 6 Drawing Sheets

U.S. PATENT DOCUMENTS

| | | | | |
|---|---|---|---|---|
| 5,736,155 | A | 4/1998 | Bally et al. | 424/450 |
| 5,753,613 | A * | 5/1998 | Ansell et al. | 514/2 |
| 5,820,873 | A | 10/1998 | Choi et al. | 424/283.1 |
| 5,837,282 | A | 11/1998 | Fenske et al. | 424/450 |
| 5,885,613 | A | 3/1999 | Holland et al. | 424/450 |
| 6,320,017 | B1 | 11/2001 | Ansell | 528/310 |

OTHER PUBLICATIONS

Bloomfield, V., "Quasi-Elastic Light Scattering Application in Biochemistry and Biology," *Ann. Rev. Biophys. Bioeng.* 10:421-450, 1981.

Burnell, E. et al., "Effects of Tumbling and Lateral Diffusion on Phosphatidylcholine Model Membrane $^{31}$P-NMR Lineshapes," *Biochim Biophys Acta* 603(1):63-69, Dec. 1980.

Cullis, P. et al., Polymorphic Phase Behaviour of Lipid Mixtures as detected by $^{31}$P NMR. Evidence that Cholesterol may Destabilize Bilayer Structure in Membrane Systems Containing Phosphatidylethanolamine, *Biochim. Biophys Acta* 507(2):207-218, Feb. 1978.

Cullis, P. et al., "The Polymorphic Phase Behaviour Of Phosphatidylethanolamines of Natural and Synthetic Origin. A $^{31}$P NMR Study," *Biochim Biophys Acta* 513(1):31-42, Oct. 1978.

Cullis, P. et al., "Polymorphic Phase Behaviour of Cardiolipin as Detected by $^{31}$P NMR and Freeze-Fracture Techniques. Effects of Calcium, Dibucaine and Chlorpromazine," *Biochim Biophys Acta* 513(1):11-20, Oct. 1978.

Cullis, P. et al., *Biochemistry of Lipids, Lipoproteins and Membranes*, (Vance et al. ed.), Elsevier, Amsterdam, 1996, Ch. 1, "Physical Properties and Functional Roles of Lipids in Membranes," pp. 1-33.

Deamer, D. et al., "Large Volume Liposomes by an Ether Vaporization Method," *Biochim Biophys Acta* 443:629-634, 1976.

Drummond, D. et al., "Current Status of pH-Sensitive Liposomes in Drug Delivery," *Progress in Lipid Research* 39(1):409-460, Sep. 2000.

U.S. Appl. No. 08/316,407, filed Sep. 30, 1994, Holland et al.

U.S. Appl. No. 08/316,394, filed Sep. 30, 1994, Ansell.

U.S. Appl. No. 08/996,783, filed Feb. 2, 1998, Ansell.

U.S. Appl. No. 09/541,436, Sarris et al.

Fiske, C. et al., "The Colorimetric Determination of Phosphorus," *J. Biol. Chem.* 66(2):375-400, 1925.

Fraley, R. et al., "Entrapment of a Bacterial Plasmid in Phospholipid Vesicles: Potential for Gene Transfer," *Proc. Natl. Acad. USA* 76(7):3348-3352, Jul. 1979.

Gerasimov, O. et al., *Vesicles*, (Rosoff ed.), Marcel Dekker, Inc., New York, 1996, "Ch. 17, triggered Release form Liposomes Mediated by Physically and Chemically Induced Phase Transitions," pp. 679-746.

Hafez, I. et al., "Tunable pH-Sensitive Liposomes Composed of Mixtures of Cationic and Anionic Lipids," *Biophysical Journal* 79:1438-1446, Sep. 2000.

Hafez, I. et al., "On the Mechanism whereby Cationic Lipids Promote Intracellular Delivery of Polynucleic Acids," *Gene Therapy* 8(15):1188-1196, Aug. 2001.

Haran, G. et al., "Transmembrane Ammonium Sulfate Gradients in Liposomes Produce Efficient and Stable Entrapment of Amphiphatic Weak Bases," *Biochim Biophys Acta* 1151(2):201-215, Sep. 1993.

Hayashi, H. et al., "Temperature-Controlled Release Property Of Phospholipid Vesicles Bearing A Thermo-Sensitive Polymer," *Biochim Biophys Acta* 1280(1):127-134, Apr. 1996.

Heath, T., "Covalent Attachment of Proteins to Liposomes," *Methods in Enzymology* 149:111-119, 1987.

Holland, J. et al., "Poly(ethylene glycol)-Lipid Conjugates Regulate the Calcium-Induced Fusion of Liposomes Composed of Phosphatidylethanolamine and Phophatidylserine," *Biochemistry* 35(8):2618-2624, Feb. 1996.

Holland, J. et al., "Poly(ethylene glycol)-Lipid Conjugates Promote Bilayer Formation In Mixtures Of Non-Bilayer-Forming Lipids," *Biochemistry* 35(8):2610-2617, Feb. 1996.

Hope, et al., "$Ca^{2+}$ and pH Induced Fusion of Small Unilamellar Vesicles Consisting of Phosphatidylethanolamine and Negatively Charged Phospholipids: A Freeze Fracture Study," *Biochem Biophys Res Commun.* 110(1):15-22, Jan. 1983.

Hope, M. et al., "Production of Large Unilamellar Vesicles by a Rapid Extrusion Procedure. Characterization of Size Distribution, Trapped Volume and Ability to Maintain a Membrane Potential," *Biochim. et Biophys. Acta* 812:55-65, 1985.

Hope et al., "Generation of Multilamellar and Unilamellar Phospholipid Vesicles," *Chem. and Phys. of Lipids* 40:89-107, 1986.

Hyde, S. et al., "Correction of the Ion Transport Defect in Cystic Fibrosis Transgenic Mice by Gene Therapy," *Nature* 362(6417):250-255, Mar. 1993.

Juliano, R. et al., "The Effect of Particle Size and Charge on the Clearance Rates of Liposomes and Liposome Encapsulated Drugs," *Biochem Biophys Res Commun.* 63(3): 651-658, Apr. 1975.

King, R.E., *Remington's Pharmaceutical Sciences*, 17$^{th}$ Ed., Mack Publishing Co., Philadelphia, PA, 1985, Part 8, "Pharmaceutical Preparations and Their Manufacture," pp. 1409-1677.

Lai, M-Z. et al., "Acid- and Calcium-Induced Structural Changes in Phosphatidylethanolamine Membranes Stabilized by Cholesteryl Hemisuccinate," *Biochemistry* 24(7): 1654-61, Mar. 1985.

Leonetti, J-P. et al., "Antibody-Targeted Liposomes Containing Oligodeoxyribonucleotides Complementary to Viral RNA Selectively Inhibit Viral Replication," *Proc. Natl. Acad. Sci. USA* 87:2448-2451, Apr. 1990.

Marchi-Artzner, V. et al., "Interaction, Lipid Exchange, and Effect of Vesicle Size in Systems of Oppositely Charged Vesicles," *J. Phys. Chem.* 100:13844-13856, 1996.

Mayer, L. et al., "Vesicles of Variable Sizes Produced by a Rapid Extrusion Procedure," *Biochim. et Biophys. Acta* 858:161-168, 1986.

Ostre, M.J. (ed.), *Liposomes: From Biophysics to Therapeutics*, Marcel Dekker, New York, 1993, Chapter 1, "Materials Properties of Liposomal Bilayers," pp. 1-38.

Pantazatos, D., et al., "Directly Observed Membrane Fusion Between Oppositely Charged Phospholipid Bilayers," *J Membr Biol.* 170(1): 27-38, Jul. 1999.

Pick, U., "Liposomes with Large Trapping Capacity Prepared by Freezing and Thawing of Sonicated Phospholipid Mixtures," *Archives of Biochemistry and Biophysics* 212(1):186-194, Nov. 1981.

Renk, G. et al., "Analogue Pigment Studies of Chromophore-Protein Interactions in Metarhodopsins," *Biochemistry* 28(2):907-912, Nov. 1989.

Renneisen, K. et al., "Inhibition of Expression of Human Immunodeficiency Virus-1 in Vitro by Antibody-Targeted Liposomes Containing Antisense RNA to the env Region," *J. Biol. Chem.* 265(27):16337-16342, Sep. 1990.

Stamatatos, L. et al., "Interactions of Cationic Lipid Vesicles with Negatively Charged Phospholipid Vesicles and Biological Membranes," *Biochemistry.* 27(11):3917-25, May 1988.

Straubinger, R., "pH-Sensitive Liposomes for Delivery of Macromolecules into Cytoplasm of Cultured Cells," *Methods Enzymol.* 221:361-76, 1993.

Szoka F., "Comparative Properties and Methods of Preparation of Lipid Vesicles (Liposomes)," *Ann. Rev. Biophys. Bioeng.* 9:467-508, 1980.

Tilcock, C. et al., "Influence of Cholesterol on the Structural Preferences of Dioleoylphosphatidylethanolamine-Dioleoylphosphatidylcholine Systems: A Phosphoru. -31 and Deuterium Nuclear Magnetic Resonance Study," *Biochemistry* 21(19):4596-601, Sep. 1982.

Wang, C-Y. et al., "pH-Sensitive Immunoliposomes Mediate Target-Cell-Specific Delivery and Controlled Expression of a Foreign Gene in Mouse," *Proc Natl Acad Sci U S A.* 84(22):7851-5, Nov. 1987.

Williams, K. et al., "Low Density Lipoprotein Receptor-Independent Hepatic Uptake of a Synthetic, Cholesterol-Scavenging Lipoprotein: Implications for the Treatment of Receptor-Deficient Atherosclerosis," *Proc. Natl. Acad. Sci. USA* 85:242-246, Jan. 1988.

\* cited by examiner

TRIGGERED RELEASE OF LIPOSOMAL DRUGS FOLLOWING MIXING OF CATIONIC AND ANIONIC LIPOSOMES

CROSS-REFERENCE TO RELATED APPLICATION

This application claims the benefit of U.S. Provisional Application No. 60/382,183 filed May 20, 2002, which application is incorporated herein by reference in its entirety.

BACKGROUND OF THE INVENTION

It is well recognized in the medical field that the most effective procedure for treating localized disease is to direct the pharmaceutical or drug agent (hereinafter "drugs") to the affected area, thereby avoiding undesirable toxic effects of systemic treatment. Techniques currently being used to deliver drugs to specific target sites within the body involve the utilization of time-release capsules or gel matrices from which drugs slowly "leak," or the use of implantable "syringes" that mechanically release drugs into muscles or into the blood stream. Another, and perhaps more effective delivery system, encompasses the use of liposomes containing the appropriate drug or chemical. The liposome with encapsulated drug is directed to the specific area of interest and, thereafter, the drug is released. The carrying out of this latter step is the most problematic and, in fact, the greatest barrier to the use of liposomes as drug carriers is making the liposomes release the drugs on demand at the target site of interest.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature, Tc. Current methods of drug delivery via liposomes require that the liposome carrier will ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposomes that exhibit regulated release properties have considerable potential for drug delivery. Continuous interest in this area has resulted in construction of liposomes that are sensitive to temperature, light, pH and other stimuli. Gerasimov, et al., M. Rosoff (Ed.), *Vesicles*, Marcel Dekker, New York, pp. 679-746, 1996. For example, sensitization of liposomes has been achieved by modification of liposomal surface with pH-sensitive or thermosensitive polymers (Hayashi, et al., *Biochim. Biophy. Acta*, 1280:127-134, 1996; and Drummond, et al., *Progress in Lipid Research*, 39:409-460, 2000) or by inclusion of ionizable charged lipids into the liposomal bilayer (Drummond, et al., *Progress in Lipid Research*, 39:409-460, 2000; Lai, et al., *Biochemistry*, 24:1654-1661, 1985; Hope, et al., *Biochem. Biophys. Res. Commun.*, 110:15-22, 1983; Straubinger, *Methods Enzymol.*, 221:361-376, 1993; Hafez, et al., *Biophys. J*, 79:1438-1446, 2000).

For instance, liposome membranes can be constructed so that they become destabilized when the environment becomes acidic near the liposome membrane (see, e.g., Proc. Natl. Acad. Sci. USA, 84:7851, 1987; *Biochemistry* 28:908, 1989). When liposomes are endocytosed by a target cell, for example, they can be routed to acidic endosomes which will destabilize the liposome and result in drug release. Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

In addition to the foregoing methods, a liposome having a predetermined phase transition temperature, Tc, above body temperature can be used to achieve active drug delivery. In this method, the body temperature will maintain the liposome below the Tc so that the liposome will not become leaky when placed in the body. This method of drug release is capable of "on demand" drug delivery since such liposomes experience a greatly increased membrane permeability at their Tc which, in turn, enables drug or chemical release. To release drugs from such phase transition liposomes when in the body, heat must be applied until the Tc is achieved. Unfortunately, the application of heat can, in itself, create problems within the body and, frequently, the adverse effects of the heat treatment outweigh the beneficial effects of using the liposome as a drug delivery vehicle. Moreover, such liposomes must be made of highly purified and expensive phase transition temperature phospholipid materials.

In view of the foregoing, there exists a need in the art for a method and means for targeted drug delivery that overcomes the disadvantages of the currently available methods and allows for a triggered, rapid release of the encapsulated drug or therapeutic agent at the target site. Specifically, a parenteral delivery system is required that would be stable in the circulation, following intravenous administration, allowing retention of encapsulated or associated drug or therapeutic agent(s). This delivery system would be capable of accumulating at a target organ, tissue or cell via either active targeting (e.g., by incorporating an antibody or hormone on the surface of the liposomal vehicle) or via passive targeting, as seen for long-circulating liposomes and then upon administration of a trigger cause the rapid release of the encapsulated drug or therapeutic contents.

The present invention fulfills these needs and provides further related advantages.

BRIEF SUMMARY OF THE INVENTION

The present invention provides compositions, methods, and kits that provide a triggered, rapid release of an encapsulated drug or other therapeutic agent from a liposome. In one of its aspect the invention a first liposome of one charge and a second liposome of the opposite charge are administered separately to a subject. Either or both the first or second liposome may encapsulate the drug or therapeutic agent. The first liposome and the second liposome incorporate at least one lipid in their bilayer structure which lipid which lipid taken alone would favor a non-lamellar phase under physiological conditions.

When the first and second liposome come into contact with each other, their liposome bilayer structures are disrupted causing the release of the encapsulated drug or therapeutic agent. When administered to a subject, the interval between the administration of the first and second liposomes controls when the encapsulated drug will be released. The interval may be of a suitable length to allow time for the desired biodistribution or other targeted delivery of the first-administered liposome or the interval may be according to the health status of the patient near or subsequent to the first administration of a liposome or according to the free concentrations of the drug or therapeutic agent in a tissue. The timing and amount of the second liposome to be administered can be adjusted to control the amount of the encapsulated drug or therapeutic agent to be released. The first and second liposome may be provided in the form of a kit.

In one embodiment, the first liposome is a cationic liposome and the second liposome is an anionic liposome each comprising at least one lipid in their bilayer structure which lipid taken alone would favor a non-lamellar phase under physiological conditions but which in the presence of other components can exist in a bilayer structure. In a further embodiment the first and second liposomes comprise DOPE or cholesterol in amounts which do not prevent formation of the lamellar structure. Preferably, the DOPE is in an amount of about at least 4 mole %. Preferably, the cholesterol is in an amount greater than 10 mole %, and more preferably in an amount of at least 17 mole %.

In one embodiment, the invention provides a kit comprising a first container holding a pharmaceutical composition of a charged first liposome according to the invention and a second container holding a pharmaceutical composition of a second oppositely charged liposome according to the invention. Either or both the first or second liposome may contain one or more therapeutic agents.

In another of its aspects, the invention provides coated liposomes and methods for using such liposomes in delivering drugs and therapeutic agents. Liposome charge is an important determinant in liposome clearance from the blood, with negatively charged liposomes being taken up more rapidly by the reticuloendothelial system (Juliano, Biochem. Biophys. Res. Commun. 63:651, 1975) and, thus, having shorter half-lives in the bloodstream. Liposomes with prolonged circulation half-lives are typically desirable for therapeutic and diagnostic uses. To maximize circulation half-lives, the bilayer stabilizing component is a hydrophilic polymer, e.g., PEG, conjugated to lipid anchors, e.g., PEs, having long, saturated hydrocarbon chains (C18>C16>C14) as these conjugates provide a longer lasting steric barrier. As such, by varying the charge in addition to the foregoing factors, one of skill in the art can regulate the rate at which the liposomes of the present invention become fusogenic (see, for instance, U.S. Pat. No. 5,885,613 issued on Mar. 23, 1999 and herein incorporated by reference in its entirety). The interactions between the oppositely charged liposomes (e.g., LUV) and subsequent release of drug can be inhibited by the presence of a suitable coating, such as a large hydrophilic polymer (e.g., PEG). In a preferred embodiment therefore the coating is PEG. In a more preferred embodiment, the PEG coating is covalently attached to ceramide as PEG-ceramide.

Embodiments achieving time-dependent triggered release are provided. One embodiment involves co-administering PEG-coated populations of cationic and anionic LUV, one or both of which contains the drug, and relying on the dissociation of the PEG-lipid to render the systems vulnerable to interaction and drug release. Alternatively, in a second embodiment the drug could be encapsulated in PEG-coated cationic LUV and drug release trigerred by interaction with the negatively charged constituents associated with the membranes of cells in vivo, following dissociation of the PEG coat.

In both its aspects, the charged liposomes of the present invention are ideally suited to a number of therapeutic, research and commercial applications. In therapeutic applications, for example, the first administered charged liposome is allowed to achieve access to target organs or cells before the administration of the second oppositely charged liposome. Upon contact of the oppositely charged liposomes in the body, the encapsulated drug can be released in a more targeted and time-controlled fashion.

In addition, the charged liposomes of the present invention can be used to deliver drugs, peptide, proteins, RNA, DNA or other bioactive molecules to the target cells or organs of interest.

As such, in another embodiment, the present invention provides a method for delivering a therapeutic compound to a target cell at a predetermined rate, the method comprising: first administering to a host containing the target cell a first charged liposome which comprises a lipid capable of adopting a non-lamellar phase, yet capable of assuming a bilayer structure in the presence of a second component, and a therapeutic compound or a pharmaceutically acceptable salt thereof. Subsequent to the first administration, a second and oppositely charged liposome is administered. Preferably, the second liposome is identical to the first except that an anionic lipid is used in place of a cationic lipid. Preferably, the liposomes are coated with PEG or similar substance to inhibit interaction. Administration may be by a variety of routes, but the therapeutic compounds are preferably given intravenously or parenterally. The liposomes administered to the host may be unilamellar, including liposomes having a mean diameter of 0.05 to 0.45 microns, more preferably from 0.05 to 0.2 microns.

Other features, objects and advantages of the invention and its preferred embodiments will become apparent from the attached drawings and following detailed description.

BRIEF DESCRIPTION OF THE DRAWINGS

FIG. 4. The "helper" lipids DOPE and cholesterol promote the formation of the hexagonal $H_{II}$ phase structure in equimolar mixtures of anionic and cationic LUVs. $^{31}$P NMR spectra obtained from mixtures of LUVs composed of: (A) DSPC/charged lipid/Chol (34:17:50), (B) DSPC/charged lipid/Chol (34:17:50) with doxorubicin loaded into anionic LUVs, (C) DSPC/DOPE/charged lipid (66:17:17), (D) DSPC/DOPE/charged lipid (66:17:17) with doxorubicin loaded into anionic LUVs, (E) DSPC/DOPE/charged lipid/Chol (17:17:17:50), (F) DSPC/DOPE/charged lipid/Chol (17:17:17:50) with doxorubicin loaded into anionic LUVs, (G) DSPC/DOPE/charged lipid/Chol (17:17:17:50) with doxorubicin loaded into anionic LUVs and inorganic phosphate present in extraliposomal media. DOPG and DODAC were used as charged components for anionic and cationic LUVs, correspondingly.

DETAILED DESCRIPTION OF THE INVENTION

In previous work the inventors and others (Stamatatos, et al., Biochemistry, 27:3917-3925, 1988; Marchi-Artzner, et al., J. Phys. Chem., 100:13844-13856, 1996; Bailey, et al., Biochemistry, 36:1628-1634, 1997; Pantazatos, et al., J. Membr. Biol., 170:27-38, 1999; Holland, et al., Biochemistry, 35:2618-2624, 1996; Holland, et al., Biochemistry, 35:2610-2617, 1996; Hafez, et al., Gene Therapy, 8:1188-1196, 2001) have noted that addition of cationic LUV to anionic LUV results in disruption of the LUV structure as evidenced by the formation of larger structures, lipid mixing phenomena (Bailey, et al., Biochemistry, 36:1628-1634, 1997; Holland, et al., Biochemistry, 35:2618-2624, 1996; Holland, et al., Biochemistry, 35:2610-2617, 1996) and, in some cases, formation of non-bilayer structures (Hafez, et al., Biophys. J, 79:1438-1446, 2000, and Hafez, et al., Gene Therapy, 8:1188-1196, 2001).

These studies suggest that if the anionic or cationic LUV contained encapsulated drug, considerable drug release would be expected on addition of the oppositely charged LUV population. However, upon testing this hypothesis, it was surprisingly observed that the rapid release of encapsulated drug was not readily achieved by the mixing of just any two such oppositely charged liposomes.

Upon further research, it was unexpectedly discovered that it was possible to obtain the desired rapid release of the encapsulated drug if the oppositely charged liposomes incorporated substantial amounts of one or more lipids which favor the formation of non-bilayer structures such as the H11 phase in mixed lipid systems (e.g., DOPE or cholesterol). (Cullis, et al., Biochim. Biophys. Acta, 507:207-218, 1978; and Cullis, et al., Biochim. Biophys. Acta, 513:31-42, 1978).

"Liposome" "vesicle" and "liposome vesicle" will be understood by one of ordinary skill in the art to indicate structures having lipid-containing membranes enclosing an aqueous interior. The structures may have one or more lipid membranes unless otherwise indicated, although generally the liposomes will have only one membrane. Such single-layered liposomes are referred to herein as "unilamellar". Multilayer liposomes are referred to herein as "multilamellar".

The positively charged liposomes or cationic liposomes for use according to the invention can be readily made from cationic lipids, lipids which carry a net positive charge at physiological pH. Such lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy) propyl)-N,N,N-trimethylammonium chloride ("DOTAP"); 3β-(N-(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"); and N-(1,2-dimyristyloxyprop-3-yl)-N,N-dimethyl-N-hydroxyethyl ammonium bromide ("DMRIE"). Additionally, a number of commercial preparations of cationic lipids can be used, such as LIPOFECTIN (including DOTMA and DOPE, available from GIBCO/BRL), LIPOFECTAMINE (comprising DOSPA and DOPE, available from GIBCO/BRL), and TRANSFECTAM (comprising DOGS, in ethanol, from Promega Corp.).

The anionic or negatively charged liposomes of the invention, can readily be made from anionic lipids which carry a negative net charge under physiological conditions. Such anionic lipids include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

The charged liposomes according to the invention further comprise one or more lipids which adopt a non-lamellar phase under physiological conditions, or under specific physiological conditions, e.g., in the presence of calcium ions, but which are capable of assuming a bilayer structure in the presence of a bilayer stabilizing component or a bilayer forming substance. Lipids which favor a non-lamellar phase include, but are not limited to, phosphatidylenthanolamines, ceramides, glycolipids, or mixtures thereof.

The charged liposomes of the invention preferably are coated with a hydrophillic moiety such as PEG suitable to protect the liposome from interacting with membranes or other liposomes of different charge. The PEG or other hydrophillic polymer may be covalently coupled to any lipid constituent of the liposome bilayer such as DOPE, or ceramide (e.g., dimyristoylphosphatidylethanolamine (DMPE-PEG2000), dipalmitoylphosphatidylethanolamine (DPPE-PEG2000) or distearoylphosphatidylethanolamine (DSPE-PEG2000). The PEG moeity may be of any suitable MW, including particularly molecular weights between 100 and 10,000.

The charged liposomes of the invention may comprise additional lipids including amphipathic and neutral lipids. Such lipids can be used alone or in combination, and can also include bilayer stabilizing components such as polyamide oligomers (see, e.g., U.S. patent application Ser. No. 09/218,988, "Polyamide Oligomers" by Ansell, filed Dec. 22, 1998), peptides, proteins, detergents, lipid-derivatives, such as PEG coupled to phosphatidylethanolamine and PEG conjugated to ceramides (see, U.S. patent application Ser. No. 08/485,608). In a preferred embodiment, cloaking agents, which reduce elimination of liposomes by the host immune system, can also be included, such as polyamide-oligomer conjugates, e.g., ATTA-lipids, (see, U.S. patent application Ser. No. 08/996,783, filed Feb. 2, 1998) and PEG-lipid conjugates (see, U.S. patent application Ser. Nos. 08/486,214, 08/316,407 and 08/485,608).

Any of a number of neutral lipids can be included, referring to any of a number of lipid species which exist either in an uncharged or neutral zwitterionic form at physiological pH, including diacylphosphatidylcholine, diacylphosphatidylethanolamine, ceramide, sphingomyelin, cephalin, cholesterol, cerebrosides, and diacylglycerols.

In preferred embodiments, the lipid used is sphingomyelin. In particularly preferred embodiments, the lipid comprises sphingomyelin and cholesterol.

In numerous embodiments, amphipathic lipids will be used. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palm itoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

In some embodiments, the liposomes are also fusogenic or have a fusogenic coating. Fusogenic liposomes and coatings are taught in U.S. Pat. No. 5,885,613 issued Mar. 23, 1999, herein incorporated by reference in its entirety.

The liposomes used in the present invention can be multilamellar or unilamellar, which can be formed using the methods disclosed herein and other methods known to those of skill in the art.

In certain embodiments, it is desirable to target the liposomes of this invention using targeting moieties that are specific to a cell type or tissue. Targeting of liposomes using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044, the teachings of which are incorporated herein by reference). The targeting moieties can comprise the entire protein or fragments thereof.

Targeting mechanisms generally require that the targeting agents be positioned on the surface of the liposome in such a manner that the target moiety is available for interaction with the target, for example, a cell surface receptor. The liposome is designed to incorporate a connector portion into the membrane at the time of liposome formation. The connector portion must have a lipophilic portion that is firmly embedded and anchored into the membrane. It must also have a hydrophilic portion that is chemically available on the aqueous surface of the liposome. The hydrophilic portion is selected so as to be chemically suitable with the targeting agent, such that the portion and agent form a stable chemical bond. Therefore, the connector portion usually extends out from the liposomal surface and is configured to correctly position the targeting agent. In some cases, it is possible to attach the target agent directly to the connector portion, but in many instances, it is more suitable to use a third molecule to act as a "molecular bridge." The bridge links the connector portion and the target agent off of the surface of the liposome, thereby making the target agent freely available for interaction with the cellular target.

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.,* 265:16337-16342, 1990, and Leonetti, et al., *Proc. Natl. Acad. Sci (USA),* 87:2448-2451, 1990. Other examples of antibody conjugation are disclosed in U.S. patent application Ser. No. 08/316,394 filed Sep. 30, 1994, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes,* 149 *Methods in Enzymology* 111-119, Academic Press, Inc. 1987). Other targeting methods include the biotin-avidin system.

A variety of methods are available for preparing liposomes as described in, e.g., Szoka, et al., *Ann. Rev.* Biophys. Bioeng., 9:467, 1980; U.S. Pat. Nos. 4,186,183, 4,217,344, 4,235,871, 4,2619975, 4,485,054, 4,501,728, 4,774,085, 4,837,028, and 4,946,787; PCT Publication No. WO 91/17424; Deamer and Bangham, *Biochim. Biophys. Acta,* 443:629-634, 1976; Fraley, et al., *Proc. Natl. Acad. Sci. USA,* 76:3348-3352, 1979; Hope, et al., *Biochim. Biophys. Acta,* 812:55-65, 1985; Mayer, et al., *Biochim. Biophys. Acta,* 858:161-168, 1986; Williams, et al., *Proc. Nail. Acad. Sci.,* 85:242-246, 1988; the text *Liposomes,* Marc J. Ostro, ed., Marcel Dekker, Inc., New York, 1983, Chapter 1; and Hope, et al., *Chem. Phys. Lip.,* 40:89, 1986, all of which are incorporated herein by reference. Suitable methods include, but are not limited to, sonication, extrusion, high pressure/homogenization, microfluidization, detergent dialysis, calcium-induced fusion of small liposome vesicles, and ether-infusion methods, all of which are well known in the art.

One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents, such as deoxycholate.

Unilamellar vesicles can be prepared by sonication or extrusion. Sonication is generally performed with a tip sonifier, such as a Branson tip sonifier, in an ice bath. Typically, the suspension is subjected to severed sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass. Unilamellar vesicles can also be made by dissolving phospholipids in ethanol and then injecting the lipids into a buffer, causing the lipids to spontaneously form unilamellar vesicles. Also, phospholipids can be solubilized into a detergent, e.g., cholates, Triton X, or n-alkylglucosides. Following the addition of the drug to the solubilized lipid-detergent micelles, the detergent is removed by any of a number of possible methods including dialysis, gel filtration, affinity chromatography, centrifugation, and ultrafiltration.

Following liposome preparation, the liposomes which have not been sized during formation may be sized to achieve a desired size range and relatively narrow distribution of liposome sizes. A size range of about 0.2-0.4 microns allows the liposome suspension to be sterilized by filtration through a conventional filter. The filter sterilization method can be carried out on a high through-put basis if the liposomes have been sized down to about 0.2-0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.*, 10:421-450, 1981, incorporated herein by reference. Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve gradual reduction in liposome size. For use in the present invention, liposomes having a submicron size are preferred; in particular sizes ranging from about 0.05 microns to about 0.40 microns are preferred. In particularly preferred embodiments, liposomes are between about 0.05 and about 0.2 microns.

In preferred embodiments, empty liposomes are prepared using conventional methods known to those of skill in the art.

Typically, as discussed infra, the liposomes used in the present invention will comprise a transmembrane potential, whereby drugs or other therapeutic agents are effectively loaded into and retained by the liposome. In preferred embodiments, the potential will be effected by creating a pH gradient across the membrane. In particularly preferred embodiments, the pH is lower at the interior of the liposomes than at the exterior. Such gradients can be achieved, e.g., by formulating the liposomes in the presence of a buffer with a low pH, e.g., having a pH between about 2 and about 6, and subsequently transferring the liposomes to a higher pH solution. In preferred embodiments, the pH is between about 3 and 5, and in most preferred embodiments, the pH is about 4. Any of a number of buffers can be used, such as citrate.

Subsequently, before or after sizing, the external pH can be raised, e.g., to about 7 or 7.5, by the addition of a suitable buffer, such as a sodium phosphate buffer. Raising the external pH creates a pH gradient across the liposomal membrane, thereby promoting efficient drug loading and retention.

Liposomes prepared according to these methods can be stored for substantial periods of time prior to drug loading and administration to a patient. For example, liposomes can be dehydrated, stored, and subsequently rehydrated, loaded with one or more vinca alkaloids, and administered. Dehydration can be accomplished, e.g., using standard freeze-drying apparatus, i.e., they are dehydrated under low pressure conditions. Also, the liposomes can be frozen, e.g., in liquid nitrogen, prior to dehydration. Sugars can be added to the liposomal environment, e.g., to the buffer containing the liposomes, prior to dehydration, thereby promoting the integrity of the liposome during dehydration. See, e.g., U.S. Pat. No. 5,077,056 or 5,736,155.

In numerous embodiments, the empty liposomes are first formulated in low pH buffer, and then manipulated in one of a variety of ways to obtain liposomes of the desired size. Methods for sizing liposomes include sonication, by bath or by probe, or homogenization. Preferably, following such treatments, the liposomes are between about 0.05 to 0.45 microns. Most preferably, the liposomes are between about 0.05 and about 0.2 microns. Such sized liposomes can then be sterilized by filtration. Also, particle size distribution can be monitored by conventional laser-beam particle size discrimination or the like. In addition, methods of reducing liposome sizes to a relatively well defined size distribution are known, e.g., one or more cycles of extrusion of the liposomes through a small-pore polycarbonate membrane or an asymmetric ceramic membrane.

Any variety of drugs which are selected to be an appropriate treatment for the disease to be treated in the tissue can be administered using the charged liposomes of the present invention. Often the drug will be an antineoplastic agent, such as vincristine, doxorubicin, cisplatin, bleomycin, cyclophosphamide, methotrexate, streptozotocin, and the like. It may also be desirable to deliver anti-infective agents to specific tissues by the present methods. The compositions of the present invention can also be used for the selective delivery of other drugs including, but not limited to local anesthetics, e.g., dibucaine and chlorpromazine; beta-adrenergic blockers, e.g., propranolol, timolol and labetolol; anti-hypertensive agents, e.g., clonidine and hydralazine; anti-depressants, e.g., imipramine, amitriptyline and doxepim; anti-convulsants, e.g., phenyloin; antihistamines, e.g., diphenhydramine, chlorphenirimine and promethazine; anti-bacterial agents, e.g., gentamycin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, anti-diabetic agents, antiglaucoma agents, vitamins, narcotics, and imaging agents. Other particular drugs which can be selectively administered by the compositions of the present invention will be well known to those of skill in the art. Additionally, two or more therapeutic agents may be administered simultaneously if desired, where such agents produce complementary or synergistic effects or would benefit the same condition.

A wide variety of therapeutic compounds/agents may be delivered by the liposomes and methods of the present invention. Therapeutic compound is meant to also include, e.g., nucleic acids, proteins, peptides, oncolytics, anti-infectives, anxiolytics, psychotropics, ionotropes, toxins such as gelonin and inhibitors of eucaryotic protein synthesis, and the like. Particularly preferred among the therapeutic compounds for entrapment in the liposomes of the present invention are those which are lipophilic cations. Among these are therapeutic agents of the class of lipophilic molecules which are able to partition into the lipid bi-layer phase of the liposome, and which therefore are able to associate with the liposomes in a membrane form. Representative drugs include prostaglandins, amphotericin B, methotrexate, cis-platin and derivatives, vincristine, vinblastine, progesterone, testosterone, estradiol, doxorubicin, epirubicin, beclomethasone and esters, vitamin E, cortisone, dexamethasone and esters, betamethasone valerete and other steroids, etc.

Particularly preferred therapeutic compounds for use in the present invention are the alkaloid compounds and their derivatives. U.S. patent application Ser. No. 09/541,436 filed Mar. 31, 2000, assigned to the same assignee as the present application and incorporated herein by reference, teaches preferred therapeutic agents and combinations of agents according to the invention. Among these are the members of the vinca alkaloids and their semisynthetic derivatives, such as, e.g., vinblastine, vincristine, vindesin, etoposide, etoposide phosphate, and teniposide. Among this group vinblastine and vincristine are particularly preferred. Other alkaloids useful in the present invention include paclitaxel (taxol) and synthetic derivatives thereof.

For the delivery of therapeutic agents, the charged liposomes of the present invention can be loaded with a therapeutic agent and administered to the subject requiring treatment. The therapeutic agents which can be administered using the charged liposomes of the present invention can be any of a variety of drugs, peptides, proteins, DNA, RNA or other bioactive molecules. Moreover, cationic lipids may be used in the delivery of therapeutic genes or oligonucleotides intended to induce or to block production of some protein within the cell. Nucleic acid is negatively charged and must be combined with a positively charged entity to form a complex suitable for formulation and cellular delivery.

Cationic lipids have been used in the transfection of cells in vitro and in vivo (Wang, C-Y, Huang L., "pH sensitive immunoliposomes mediate target cell-specific delivery and controlled expression of a foreign gene in mouse," *Proc. Natl. Acad. Sci. USA,* 84:7851-7855, 1987; and Hyde, S. C., Gill, D. R., Higgins, C. F., et al., "Correction of the ion transport defect in cystic fibrosis transgenic mice by gene therapy," *Nature,* 362:250-255, 1993). The efficiency of this transfection has often been less than desired, for various reasons. One is the tendency for cationic lipids complexed to nucleic acid to form unsatisfactory carriers. These carriers are improved by the inclusion of PEG (polyethylene glycol) lipids.

Cationic lipids useful in producing lipid based carriers for gene and oligonucleotide delivery include, but are not limited to, 3â-(N-(N',N'-dimethylaminoethane)carbamoyl)cholesterol (DC-Chol); N,N-distearyl-N,N-dimethylammonium bromide (DDAB); N-(1,2-dimyristyloxyprop-3-yl)-N,N-dimethyl-N-hydroxyethyl ammonium bromide (DMRIE); diheptadecylamidoglycyl spermidine (DOGS); N-(-(2,3-dioleyloxy)propyl)-N-(2-(sperminecarboxamido)ethyl)-N, N-dimethylammonium trifluoroacetate (DOSPA); N-(1-(2,3-dioleoyloxy)propyl)-N,N,N-trimethylammonium chloride (DOTAP); N-(1-(2,3-dioleyloxy)propyl)-N,N,N-trimethylammonium chloride (DOTMA); N,N-dioleyl-N,N-dimethylammonium chloride (DODAC); LIPOFECTIN, a commercially available cationic lipid comprising DOTMA and DOPE (GIBCO/BRL, Grand Island, N.Y.) (U.S. Pat. Nos. 4,897,355; 4,946,787; and 5,208,036 issued to Epstein, et al.); LIPOFECTACE or DDAB (dimethyldioctadecyl ammonium bromide) (U.S. Pat. No. 5,279,883 issued to Rose); LIPOFECTAMINE, a commercially available cationic lipid composed of DOSPA and DOPE (GIBCO/BRL, Grand Island, N.Y.); TRANSFECTAM, a commercially available cationic lipid comprising DOGS (Promega Corp., Madison, Wis.).

Any of a number of methods can be used to load the drugs or therapeutic agents into the liposomes. Such methods include, e.g., an encapsulation technique and a transmembrane potential loading method. Such methods are taught in U.S. application Ser. No. 09/541,436 filed Mar. 31, 2000 and in U.S. Pat. No. 5,532,152, both of which are incorporated herein by reference.

In one encapsulation technique, the drug and liposome components are dissolved in an organic solvent in which all species are miscible and concentrated to a dry film. A buffer is then added to the dried film and liposomes are formed having the drug incorporated into the vesicle walls. Alternatively, the drug can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers. The resulting liposomes encompassing the drug can then be sized as described above.

Transmembrane potential loading has been described in detail in U.S. Pat. Nos. 4,885,172; 5,059,421; 5,171,578; and 5,837,282 (which teaches ionophore loading), each of which is incorporated herein by reference. Briefly, the transmembrane potential loading method can be used with essentially any conventional drug which can exist in a charged state when dissolved in an appropriate aqueous medium. Preferably, the drug will be relatively lipophilic so that it will partition into the liposome membranes. A transmembrane potential is created across the bilayers of the liposomes or protein-liposome complexes and the drug is loaded into the liposome by means of the transmembrane potential. The transmembrane potential is generated by creating a concentration gradient for one or more charged species (e.g., $Na^+$, $K^+$, and/or $H^+$) across the membranes. This concentration gradient is generated by producing liposomes having different internal and external media and has an associated proton gradient. Drug accumulation can then occur in a manner predicted by the Henderson-Hasselbach equation.

As known to one of ordinary skill in the art, the charged liposomes of the invention can be administered in any of a number of ways, including parenteral, intravenous, systemic, local, intratumoral, intramuscular, subcutaneous, intraperitoneal, inhalation, or any such method of delivery. In preferred embodiments, the pharmaceutical compositions are administered intravenously by injection. For instance, the liposomes may be administered by parenteral routes. These include intravenous, intramuscular, subcutaneous, and intraarterial. Generally, the liposomes will be administered intravenously or in some cases via inhalation. Often, the liposomes will be administered into a large central vein, such as the superior vena cava or inferior vena cava, to allow highly concentrated solutions to be administered into large volume and flow vessels. The liposomes may be administered intraarterially following vascular procedures to deliver a high concentration directly to an affected vessel. In some instances, the liposomes may be administered orally or transdermally, although the advantages of the present invention are best realized by parenteral administration. The liposomes may also be incorporated into implantable devices for long duration release following placement.

Suitable formulation for use in the present invention can be found, e.g., in *Remington's Pharmaceutical Sciences*, Mack Publishing Company, Philadelphia, Pa., 17$^{th}$ Ed., 1985. Often, intravenous compositions will comprise a solution of the liposomes suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) will be used. These compositions can be sterilized by conventional sterilization techniques, such as filtration. The compositions may contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, triethanolamine oleate, etc. These compositions can be sterilized using the techniques referred to above, or can be produced under sterile conditions. The concentration of liposomes in the carrier can vary. Generally, the concentration will be about 20-200 mg/mL, however persons of skill can vary the concentration to optimize treatment with different liposome components or for particular patients. For example, the concentration may be increased to lower the fluid load associated with treatment.

The amount of the drug or therapeutic agent administered per dose is selected to be above the minimal therapeutic dose. The choice of amount per dose will depend on a number of factors, such as the medical history of the patient, the use of other therapies, and the nature of the disease or condition to be treated.

Patients typically will be administered two liposome compositions. A first charged composition will be administered prior to the administration of the second oppositely charged liposome composition. Either one or both the compositions will contain a drug or therapeutic agent. The interval between administration may be according to the time required for biodistribution of the first administered liposome, the condition of the patient, or the tissue levels (e.g., blood, target organ) of the therapeutic agent of interest.

As described above, the liposomes will generally be administered intravenously or via inhalation in the methods of the present invention. Often multiple treatments will be given to the patient. The dosage schedule of the treatments will be determined by the disease and the patient's condition. Standard treatments with therapeutic compounds that are well known in the art may serve as a guide to treatment with liposomes containing the therapeutic compounds. The duration and schedule of treatments may be varied by methods well known to those of skill, but the increased circulation time and decreased in liposome leakage will generally allow the dosages to be adjusted downward from those previously employed. The dose of liposomes of the present invention may vary depending on the clinical condition and size of the animal or patient receiving treatment. The standard dose of the therapeutic compound when not encapsulated may serve as a guide to the dose of the liposome-encapsulated compound. The dose will typically be constant over the course of treatment, although in some cases the dose may vary. Standard physiological parameters may be assessed during treatment that may be used to alter the dose of the liposomes of the invention.

The following example is offered by way of illustration, not limitation.

EXAMPLE

This example illustrates the influence of dioleoylphosphatidylethanolamine (DOPE) and cholesterol, two lipids that have been shown to favour or facilitate formation of non-bilayer structures such as the inverted hexagonal ($H_{II}$) phase. Employing anionic doxorubicin-containing LUV, it has been found that rapid release of encapsulated doxorubicin can be achieved on addition of cationic LUV and that this rapid release correlates with formation of nonbilayer lipid structures demonstrated by $^{31}P$ NMR and freeze-fracture techniques. Further, the presence of both DOPE and cholesterol is surprisingly essential for rapid release to be observed. These results are discussed below in terms of the potential utility of these systems for triggered release applications.

N,N-dimethyl-N,N-di-9-cis-octadecenylammonium chloride (DODAC) was provided by Dr. J. Gaucheron, University of British Columbia (Vancouver, BC, Canada). 1,2-Dioleoyl-sn-glycero-3-phosphoglycerol (DOPG), 1,2-distearoyl-sn-glycero-3-phosphocholine (DSPC) and 1,2-dioleoyl-sn-glycero-3-phosphoethanolamine (DOPE) were obtained from Avanti Polar Lipids (Alabaster, Ala.). Cholesterol (Chol) and doxorubicin hydrochloride were purchased from Sigma Chemical Company (St. Louis, Mo.). 1-O-(2'-(ω-methoxypolyethylene-glycol)succinoyl)-2-N-myristoylsphyngosine (PEG-CerC$_{14}$) was obtained from Inex Pharmaceuticals (Burnaby, BC, Canada). All other reagents used in this study were of analytical grade.

Aqueous dispersions of lipids were obtained by hydrating a lipid film, which was prepared by co-dissolving lipids to desired molar ratios and drying under a nitrogen stream followed by the removal of residual solvent under high vacuum. Dried lipid films were hydrated with 300 mM aqueous solution of ammonium sulfate or 150 mM saline with five freeze-thaw cycles (liquid $N_2$/60° C.) to give multilamellar vesicle (MLV) suspensions. Large unilamellar vesicles (LUV) were generated by extrusion of MLVs through two stacked Nuclepore polycarbonate filters with a pore size of 100 nm (10 passes) using extrusion device obtained from Lipex Biomembranes (Vancouver, BC, Canada). All preparations were extruded at temperatures above the gel-to-liquid crystalline phase transition of DSPC. The mean diameter of LUVs was determined by dynamic light scattering using a NICOMP 370 particle sizer (Nicomp Particle Sizing Inc., Santa Barbara, Calif.) and found 117±25 nm. Phospholipid concentrations were determined by established methods (Fiske, et al., *J. Biol. Chem.,* 66:375-379, 1925).

LUVs dispersed in ammonium sulfate solution were used for loading with doxorubicin (Haran, et al., *Biochim. Biophys. Acta,* 1151:201-215, 1993). An ammonium sulfate gradient was generated by exchanging the extravesicular solution with 150 mM NaCl, pH 7.4 on Sephadex G-50 spin columns (Pick, *Arch. Biochem. Biophys.,* 212:186-194, 1991). Doxorubicin hydrochloride was then added to the LUVs (5 mM total lipid) to give a molar drug-to-lipid ratio of 0.05. The samples were incubated at 60° C. for 1 h to provide optimal loading conditions. Unentrapped doxorubicin was removed by running the samples over Sephadex G-50 spin columns prior to detection of liposomally entrapped drug.

To estimate the percentage of doxorubicin leakage from liposomes, an aliquot of liposomal doxorubicin was diluted 500-fold by injection into a cuvette containing 150 mM saline and the fluorescence intensity of doxorubicin was measured (excitation and emission wavelengths 480 and 590 nm, respectively) with a Perkin-Elmer LS50 fluorimeter (Perkin-Elmer, Norwalk, Conn.). The value for 100% leakage was obtained by addition of 10% Triton X-100 to a final concentration of 0.5%. The percentage of leakage of doxorubicin at a given time was calculated according to:

$$\% \text{ leakage} = (F - F_0)/(F_{100} - F_0) \times 100$$

where F is the fluorescence intensity of the sample at a given time, and $F_0$ and $F_{100}$ are intensities of samples before inducing of leakage or after addition of Triton X-100, respectively.

Samples were cryo-fixed in the presence of 33% glycerol by plunging them into liquid Freon 22 cooled by liquid nitrogen. The fractured surface was shadowed unidirectionally with platinum (45°) and coated with carbon (90°) employing a Balzers freeze-etching system BAF 400D (Balzers, Liechtenstein). Replicas were analysed using a JEOL model JEM 1200EX electron microscope (Soquelec, Montreal, Canada).

Proton decoupled $^{31}$P NMR spectra were obtained using a Bruker MSL-200 spectrometer operating at 81.02 MHz. Acquisition parameters included 3.0 μs 60° pulse, a spectral width of 25 kHz with 4k data points and a 1 s interpulse delay time. The sample temperature (±1° C.) was regulated using a Bruker VT-100 temperature controller. If not otherwise indicated the temperature was maintained at 25° C. An exponential multiplication corresponding to 50 Hz line broadening was applied to the free induction decays prior to Fourier transformation. The chemical shift was referenced to external 85% phosphoric acid ($H_3PO_4$).

LUVs composed of DSPC, DOPE, cholesterol and charged lipids (anionic, DOPG or cationic, DODAC) at varying ratios were used throughout these studies. Both DOPG and DODAC are permanently charged at pH 7.4 and are lipids that preferentially adopt the bilayer phase upon hydration. The presence of DOPE (which facilitates the formation of the $H_{II}$ phase) at levels up to 17% mol did not destabilize the lipid bilayer of charged LUVs at room temperature. To evaluate the effect of a poly(ethylene)glycol (PEG) coating on the interaction of oppositely charged vesicles, PEG-CerC$_{14}$ was included in some liposomal preparations.

Doxorubicin was loaded into anionic and cationic LUVs (DSPC/DOPE/charged lipid/Chol at varying mole ratios) in response to a pH gradient induced by ammonium sulfate. It was found that this method could be used for loading doxorubicin into both cationic and anionic liposomes, however the anionic liposomes were slightly more stable and thus doxorubicin was loaded into the anionic LUV in all the experiments conducted here. Efficiency of encapsulation with initial doxorubicin-to-lipid ratio=0.05 was close to 100%. No leakage of entrapped doxorubicin from anionic LUVs was observed over 1 h incubation time.

Figure 1:
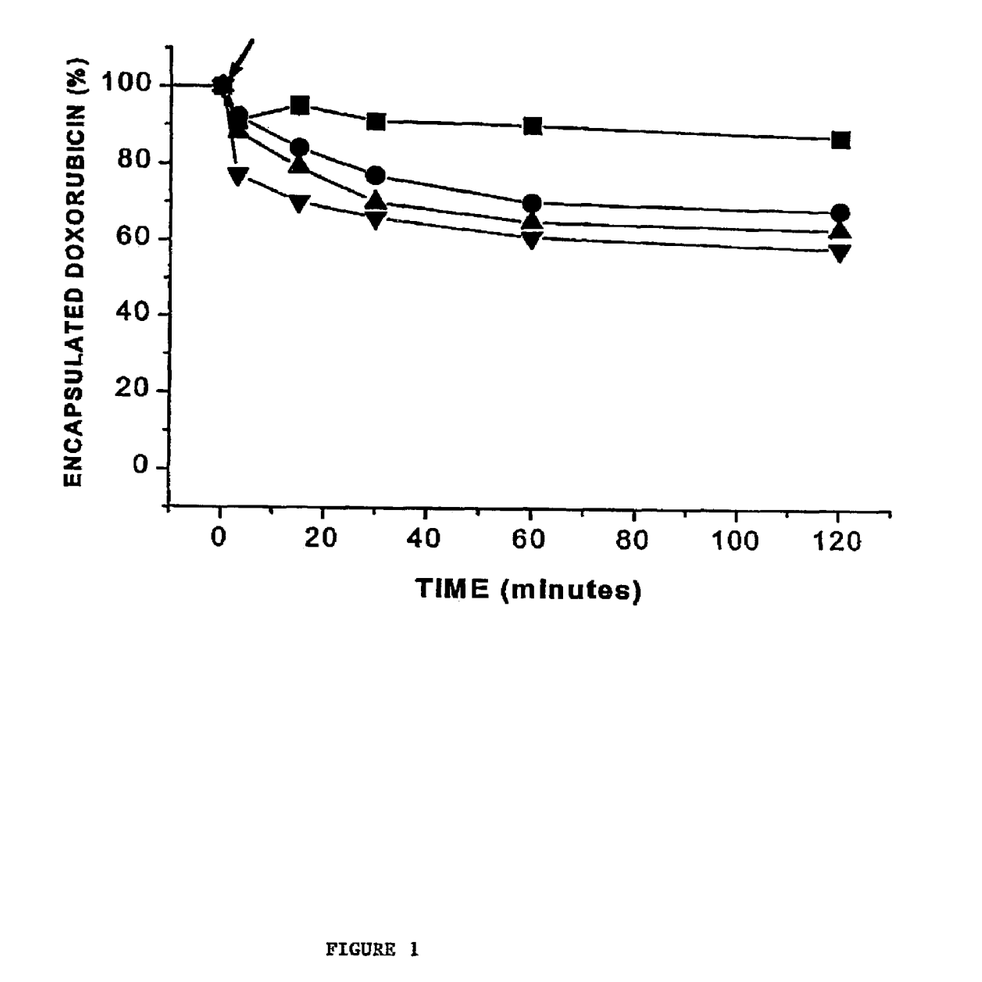
FIG. 1. Release of doxorubicin from the charged LUVs after mixing with equimolar amounts of LUVs of opposite charge. Lipid compositions: (■) DSPC/charged lipid/Chol (34:17:50), (•) DSPC/charged lipid/Chol (25:25:50), (▲)DSPC/charged lipid/Chol (30:30:40), (▼) DSPC/charged lipid/Chol (20:40:40). DOPG and DODAC were used as charged components for anionic and cationic LUVs, correspondingly. Arrow indicates the moment of mixing.

Initial studies were conducted to determine whether presence of DOPE is necessary to achieve rapid and complete release of encapsulated doxorubicin upon mixing of charged LUVs. In the first set of experiments, the effect of surface charge concentration on the extent of doxorubicin leakage in the absence of DOPE was examined. Mixing of equal volumes of DSPC/DOPG/Chol (34:17:50) and DSPC/DODAC/Chol (34:17:50) vesicles (4 mM total lipid in both populations) resulted in rapid aggregation which appeared as a transformation of the translucent LUV preparations to turbid, milky dispersion. Quasi-elastic light scattering measurements revealed formation of large aggregated structures with broad size distribution (400-600 nm). As shown in FIG. 1, these systems show some leakage of doxorubicin upon mixing where the initial rate was dependent on the charged lipid content. However, the leakage did not exceed 50% of the total encapsulated doxorubicin after 2 h incubation at 20° C.

Both DOPE and cholesterol promote the formation of non-bilayer structures such as the $H_{II}$ phase in mixed lipid systems (Hafez, et al., *Gene Therapy,* 8:1188-1196, 2001; Cullis, et al., *Biochim. Biophys. Acta,* 507:207-218, 1978; Cullis, et al., *Biochim. Biophys. Acta,* 513:31-42, 1978; and Tilcock, et al., *Biochemistry,* 21:4596-4601, 1982). If the mechanism of release involves formation of $H_{II}$ phase or related nonbilayer structures, it would be expected that inclusion of DOPE and/or cholesterol into the bilayer of the cationic and anionic liposomes should promote more extensive bilayer destabilization upon interaction, resulting in faster release.

Figure 2:
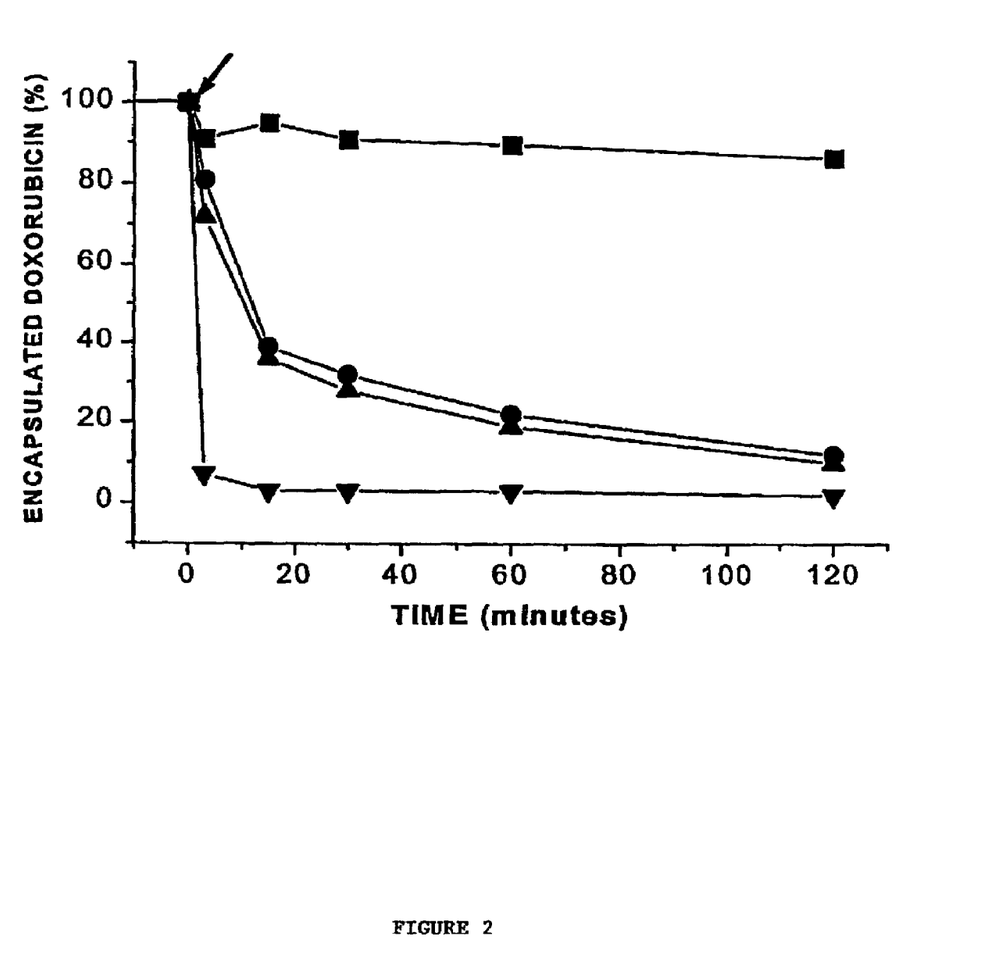
FIG. 2. Effect of DOPE on the rate of doxorubicin release from the charged LUVs after mixing with equimolar amounts of LUVs of opposite charge. Lipid compositions: (■) DSPC/charged lipid/Chol (34:17:50), (•) DSPC/DOPE/charged lipid/Chol (29:4:17:50), (▲) DSPC/DOPE/charged lipid/Chol (25:8:17:50), (▼) DSPC/DOPE/charged lipid/Chol (17:17:17:50). DOPG and DODAC were used as charged components for anionic and cationic LUVs, correspondingly. Arrow indicates the moment of mixing.

FIG. 2 shows time courses of doxorubicin leakage from DSPC/DOPE/DOPG/Chol liposomes induced by mixing with DSPC/DOPE/DODAC/Chol liposomes at varying DOPE content. Comparing these data to those shown in FIG. 1, it is apparent that the presence of DOPE remarkably enhances both the rate and the amount of doxorubicin leakage. At 17 mole % DOPE, release of 90% of the encapsulated doxorubicin was observed within 30 s after mixing. In latter case, formation of nonbilayer structures in mixed dispersions was detected using $^{31}$P NMR techniques (see Section 3.4), suggesting that the presence of DOPE is necessary for destabilization of bilayer structure. It may be noted that the interactions of the DOPE-containing LUVs giving rise to maximum doxorubicin leakage gave rise to aggregation that produced particles larger than could be measured by light scattering.

Figure 3:
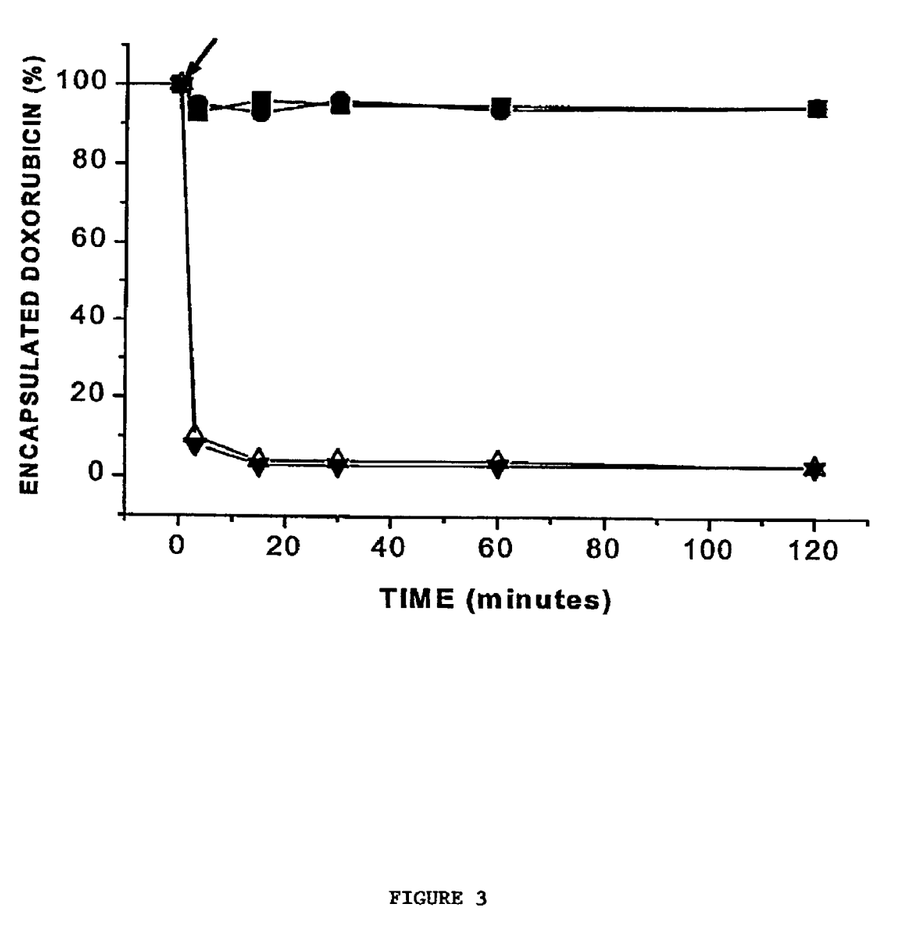
FIG. 3. Effect of cholesterol on the rate of doxorubicin release from the charged LUVs after mixing with equimolar amounts of LUVs of opposite charge. Lipid compositions: (■) DSPC/DOPE/charged lipid (66:17:17), (•) DSPC/DOPE/charged lipid/Chol (56:17:17:10), (A) DSPC/DOPE/charged lipid/Chol (50:17:17:17), (▼) DSPC/DOPE/ charged lipid/Chol (17:17:17:50). DOPG and DODAC were used as charged components for anionic and cationic LUVs, correspondingly. Arrow indicates the moment of mixing.

The effect of cholesterol on the leakage of doxorubicin from anionic DSPC/DOPE/DOPG/Chol LUVs following mixing with cationic DSPC/DOPE/DODAC/Chol LUVs is illustrated in FIG. 3. Remarkably, as the cholesterol content is increased from 10 mol % to 17 mol %, the doxorubicin leakage increases from less than 5% over 2 h to more than 90% within 30 s. It may be concluded that cholesterol is absolutely required to achieve the rapid release rates suitable for "triggered release" applications.

It is well established (Cullis, et al., J. E. Vance (Eds.), *Biochemistry of Lipids, Lipoproteins and Membranes,* Marcel Dekker, Elsevier, pp. 1-32, 1996) that phospholipids organized in (large) bilayer structures give rise to $^{31}$P NMR spectra with a characteristic asymmetric lineshape with a high field peak and a low field shoulder, displaying a residual chemical shift anisotropy of approximately −40 ppm for lipids in the liquid crystalline state. In contrast, phospholipids such as DOPE that adopt the inverted hexagonal phase in isolation exhibit reversed asymmetry compared to the "bilayer" lineshape with a chemical shift anisotropy that is a factor of two smaller than observed for bilayer spectra.

Figure 4:
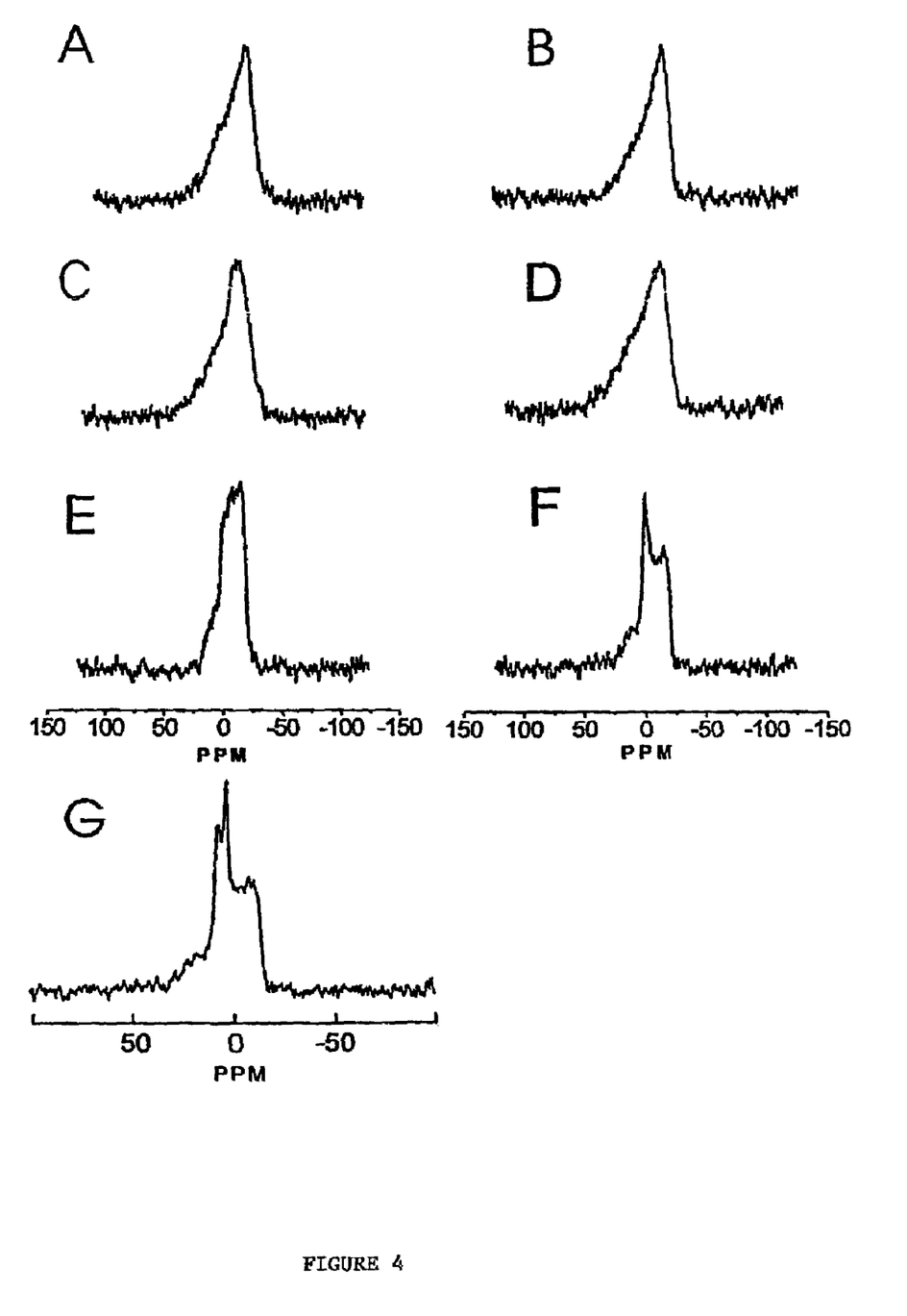

As shown in FIGS. 4 A-B, the lipid dispersion produced on mixing equimolar amounts of DSPC/DOPG/Chol (34: 17:50) and DSPC/DODAC/Chol (34:17:50) LUV reveals the $^{31}$P NMR lineshape associated with bilayer structure. Incorporation of DOPE (in absence of cholesterol) also resulted in a bilayer lineshape (FIGS. 4 C-D). However, a mixture of DSPC/DOPE/DOPG/Chol (17:17:17:50) and DSPC/DOPE/DODAC/Chol (17:17:17:50) LUVs gave rise to a spectrum in which a weak $H_{II}$ phase signal was superimposed on a bilayer signal (FIG. 4 E), suggesting that part of lipid molecules adopted the $H_{II}$ phase upon mixing. When doxorubicin was present in the anionic LUVs, a significant increase in the size of the $H_{II}$ component was observed (FIG. 4 F). In order to unambiguously establish that the superimposed $^{31}$P NMR resonance corresponded to $H_{II}$ phase lipid and not a narrow "isotropic" peak arising from small vesicles, the chemical shift of the superimposed peak was compared to that arising from inorganic phosphate (see FIG. 4 G). The chemical shift difference of 6.8 ppm is consistent with the superimposed peak arising from $H_{II}$ structure. In summary, these data show that, in systems that exhibit rapid release, the lipid dispersions obtained on mixing the anionic and cationic LUV exhibit limited $H_{II}$ phase structure. In addition, these results suggest that doxorubicin itself exerts an additional disordering effect on the lipid bilayer structure, inducing formation of larger $H_{II}$ phase domains and therefore promoting its own release.

Figure 5:
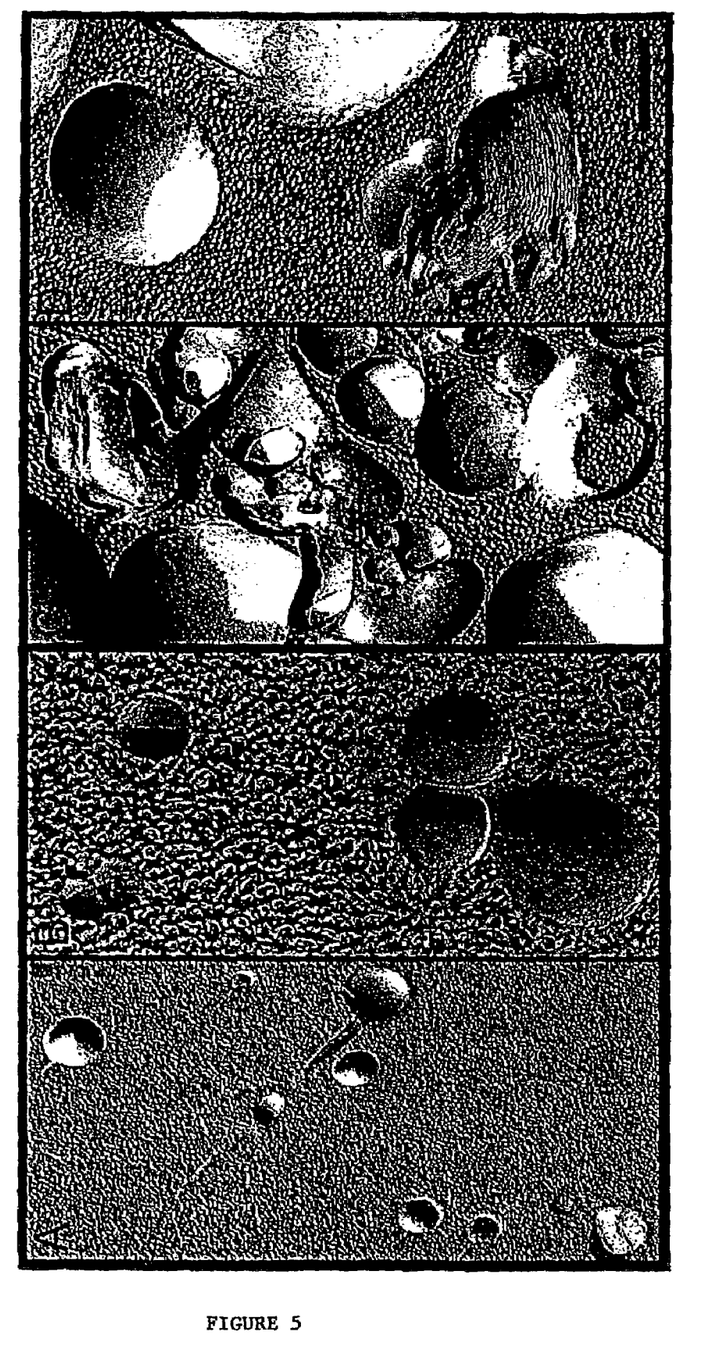
FIG. 5. Freeze-fracture electron micrographs of liposome preparations. (A) DSPC/DOPE/DOPG/Chol (17:17:17:50) formed after extrusion through two stacked filters with 0.1 µm pore size, (B) equimolar mixture of oppositely charged DSPC/DOPE/charged lipid/Chol (17:17:17:50) LUVs, (C) equimolar mixture of oppositely charged DSPC/DOPE/ charged lipid/Chol (17:17:17:50) LUVs with doxorubicin loaded into anionic LUVs, (D) formation of $H_{II}$ phase structures in mixtures DSPC/DOPE/charged lipid/Chol (17: 17:17:50) LUVs in presence of doxorubicin. Original magnification was 20000×, and bar represents 200 nm.

The structures of the dispersions formed on mixing of oppositely charged LUVs were also examined by freeze-fracture electron microscopy. It was found that mixed anionic DSPC/DOPE/DOPG/Chol (17:17:17:50) LUV (that did not contain doxorubicin) and cationic DSPC/DOPE/DODAC/Chol (17:17:17:50) LUVs predominantly form aggregates of vesicles (FIG. 5 B). However, mixing of anionic doxorubicin-loaded LUVs with cationic vesicles resulted in formation of significantly bigger aggregates and some very large particles (FIG. 5 C). Fragments of some structures reveal the characteristic striated pattern attributed to lipids organized in the hexagonal $H_{II}$ phase (FIG. 5 D). In agreement with the results obtained by $^{31}$P NMR, these data support the presence of non-bilayer $H_{II}$ phase structure in the lipid dispersions resulting from mixing cationic and anionic LUV that give rise to rapid release of encapsulated doxorubicin.

Figure 6:
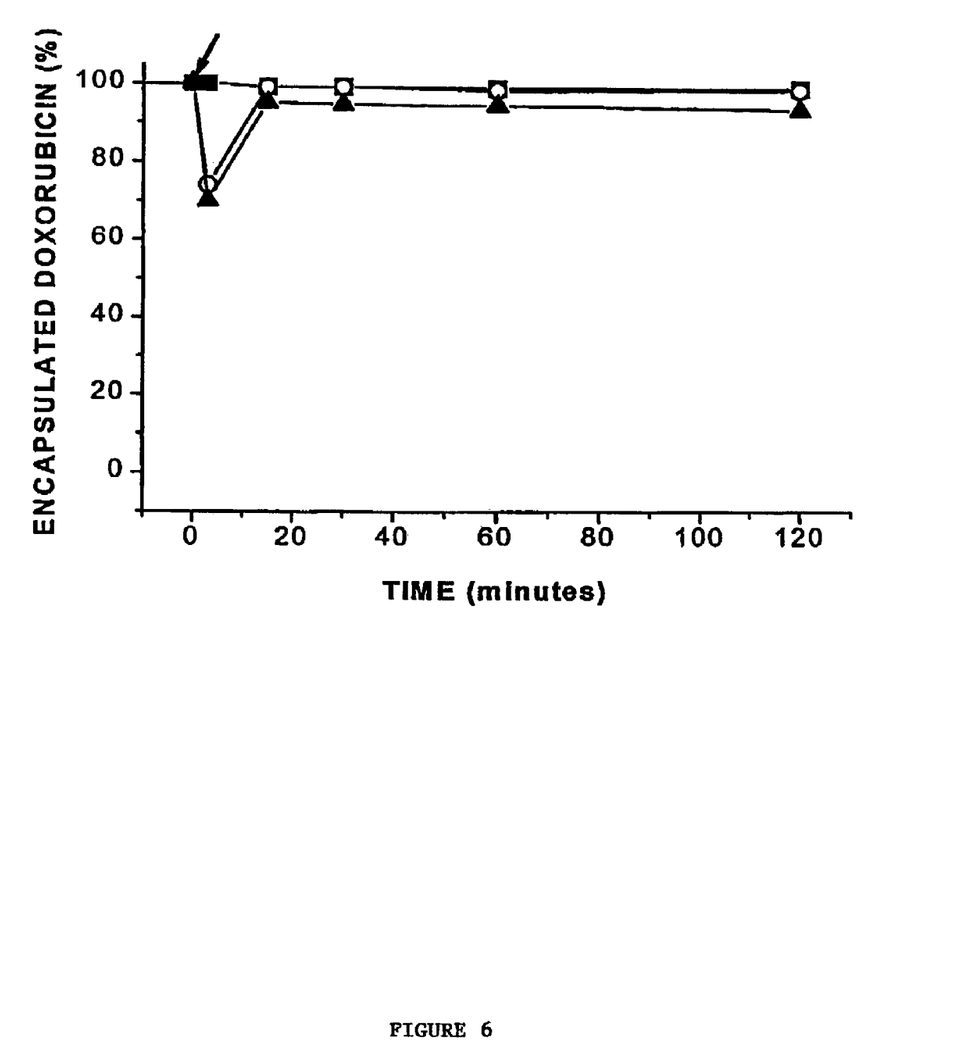
FIG. 6. Effect of PEG-CerC$_{14}$ coating on the rate of doxorubicin release from the charged LUVs after mixing with equimolar amounts of LUVs of opposite charge. Lipid compositions: (■) DSPC/DOPE/charged lipid/Chol/PEG-CerC$_{14}$ (17:17:17:50:7.5), (O) DSPC/DOPE/charged lipid/ Chol/PEG-CerC$_{14}$ (17:17:17:50:5), (▲) DSPC/DOPE/ charged lipid/Chol/PEG-CerC$_{14}$ (17:17:17:50:2.5). DOPG and DODAC were used as charged components for anionic and cationic LUVs, correspondingly. Arrow indicates the moment of mixing.

Previous studies have shown that a PEG coating can inhibit calcium-induced fusion between LUVs (Holland, et al., *Biochemistry*, 35:2618-2624, 1996). It was, therefore, of interest to determine whether incorporation of PEG could prevent release of contents upon mixing of oppositely charged LUVs. Inclusion of 7.5 mol % of PEG-CerC$_{14}$ into both cationic and anionic vesicles was found to prevent virtually any leakage of encapsulated doxorubicin following mixing (FIG. 6). However, when PEG-CerC$_{14}$ content was decreased to 5 mol %, release of about 22% of liposomal doxorubicin occurred within 30 sec after mixing. Interestingly, during the next 15 minutes of incubation quenching of doxorubicin fluorescence was observed. This effect cannot be attributed to the self-association of doxorubicin because of low concentration of the latter in the extraliposomal media. Rather, it means that considerable fraction of PEG-coated doxorubicin-containing LUVs remains unaffected, thus maintaining residual transmembrane pH gradient sufficient to re-load doxorubicin released from destabilized vesicles. Dynamic light scattering did not reveal considerable increase of particle size after mixing of LUVs with 7.5% as well as 5% PEG. When PEG content was diminished to 2.5 mol %, similar "re-loading" effect was observed, but, in this case, released doxorubicin was not completely removed from observation and liposome size and polydispersity increased from 117±30 to 155±36 nm. Thus, it was demonstrated that presence of PEG at 7.5 mol % may effectively inhibit unloading of the doxorubicin upon mixing of oppositely charged LUVs. It should be noted that inhibition of doxorubicin release upon mixing was also achieved when PEG-CerC$_{14}$ was included only into loaded LUVs at 10 mole %.

The results of this study demonstrate that relatively immediate and complete release of doxorubicin encapsulated in anionic LUV can be achieved on mixing with cationic LUV and that this release is dependent on the presence of DOPE and cholesterol. Three aspects of this work are addressed in further detail below; namely, the mechanism of drug release, the role of lipids such as DOPE and cholesterol, and the potential applications of these systems for triggered release of drug in vivo.

The mechanism whereby the addition of cationic LUV to doxorubicin-containing anionic LUV induces drug release is clearly not just due to aggregation. It may be noted that for all the systems investigated here considerable aggregation as evidenced by an increased particle size as determined by QELS occurred on addition of the cationic LUV to the anionic, drug-containing LUV. However, in the absence of DOPE and/or cholesterol little or no release of drug is observed, indicating that aggregation alone does not result in particularly rapid or complete release. Equally, however, the release cannot be correlated with fusion. The $^{31}$P NMR spectra resulting from the dispersions of cationic and anionic LUV prepared in the absence of DOPE or cholesterol are classical "bilayer" spectra consistent with lipid structures of 200 nm diameter or larger (Burnell, et al., *Biochim. Biophys. Acta*, 603:63-69, 1980), much larger than the 100 nm LUV that these structures originated from. These structures must be fused, rather than stacked, as stacked 100 nm diameter systems would be expected to give rise to considerable narrower spectra due to motional averaging effects arising from lateral diffusion processes (Burnell, et al., *Biochim. Biophys. Acta*, 603:63-69, 1980). The parameter that appears to correlate most closely with the ability of cationic LUV to cause rapid and complete release of doxorubicin entrapped in anionic LUV is the appearance of an $H_{II}$ phase component in the resulting lipid dispersion. That the presence of a local region of $H_{II}$ structure should give to rapid leakage is perhaps not unreasonable as it represents a relatively massive and long-lived perturbation of local bilayer structure.

The requirement for DOPE and cholesterol in order to achieve rapid release of doxorubicin can now retrospectively be readily understood in terms of a need for local regions of non-bilayer structure. DOPE assumes the $H_{II}$ phase in isolation and progressively promotes non-bilayer organization when incorporated in bilayer systems (Cullis, et al., *Biochim. Biophys. Acta*, 513:31-42, 1978). Similarly, cholesterol has long been noted to induce $H_{II}$ structure in mixed DOPE-DOPC system s (Tilcock, et al., *Biochemistry*, 21:4596-4601, 1982). Assuming complete mixing of lipids following addition of the cationic LUV to the anionic LUV, the lipid composition of the dispersions produced is DSPC/DOPE/DODAC/DOPG/cholesterol (1:1:0.5:0.5:x). Given that mixtures of DODAC and DOPG assume the $H_{II}$ phase organization (Hafez, et al., *Gene Therapy*, 8:1188-1196, 2001), the ratios of bilayer lipid, $H_{II}$ phase-preferring lipid and cholesterol are then 1:2:x. These previous studies have demonstrated appreciable formation of $H_{II}$ phase structure in mixed lipid systems where the ratio of bilayer lipid, $H_{II}$ phase lipid and cholesterol are 1:2:1 (Tilcock, et al., *Biochemistry*, 21:4596-4601, 1982).

There are a number of ways in which triggered release of encapsulated drug arising from mixing cationic and anionic LUV could be of utility for in vivo drug delivery applications involving the use of PEG-coated LUV systems. Briefly, the above results demonstrate that the interactions between the LUV and subsequent release of drug can be inhibited by the presence of a PEG coating. It has previously been demonstrated that the dissociation rates of PEG-Ceramides can be modulated by varying the length of the acyl chain associated with the ceramide anchor. For example, the dissociation rates increase from <1 min for $PEG-CerC_8$ to 1.2 h for $PEG-CerC_{14}$ to more than 13 d for $PEG-CerC_{20}$. Two circumstances leading to time-dependent triggered release can be envisaged. The first involves co-administering PEG-coated populations of cationic and anionic LUV, one or both of which contains the drug, and relying on the dissociation of the PEG-lipid to render the systems vulnerable to interaction and drug release. Alternatively, the drug could be encapsulated in PEG-coated cationic LUV and drug release trigerred by interaction with the negatively charged constituents associated with the membranes of cells in vivo, following dissociation of the PEG coat.

In many applications an ability of liposomes to retain drug and then rapidly release it at some later time would be of benefit. In this work, we address the ability of cationic large unilamellar vesicles (LUV) to promote rapid release of doxorubicin from anionic LUV. It is shown that the addition of cationic liposomes containing cholesterol, dioleoylphosphatidylethanolamine (DOPE), distearoylphosphatidylcholine (DSPC) and the cationic lipid N,N-dioleyl-N,N-dimethylammonium chloride (DODAC) to doxorubicin-containing LUV composed of cholesterol, DOPE, DSPC and the anionic lipid dioleoyphosphatidylglycerol (DODAC) can result in release of more than 90% of the drug in times of 30 s or less. Further, it is shown that these release characteristics are exquisitely dependent on the presence of DOPE and cholesterol. In the absence of DOPE much slower release rates are observed, with maximum release levels of only 40%. Remarkably, threshold levels of more than 10 mol % of cholesterol are required before any release is observed. $^{31}P$ NMR spectroscopy and freeze-fracture electron microscopy studies reveal that systems giving rise to rapid release of doxorubicin exhibit limited formation of inverted hexagonal ($H_{II}$) phase, suggesting that these lipids facilitate drug release by formation of local regions of non-bilayer structure. These observations demonstrate that drug release triggered by mixing anionic and cationic liposomes can be a rapid and efficient process.

Although the foregoing invention has been described in some detail by way of illustration and example for purposes of clarity of understanding, it will be apparent that certain changes and modifications may be practiced within the scope of the appended claims. Further, each of the references mentioned herein are incorporated by reference in their entirety for all purposes to the extent they are not inconsistent with the present disclosure.

We claim:

1. A method of triggering the release of a therapeutic agent in a subject, the method comprising:
   administering intravenously a first liposome loaded with the therapeutic agent to a subject, the first liposome having a net positive or negative charge and comprising dioleoylphosphatidylethanolamine (DOPE) in an amount of at least 4 mole % and cholesterol in an amount of at least 10 mole %; and
   administering intravenously a trigger to the subject, the trigger comprising a second liposome having a net charge opposite to the first liposome and comprising DOPE in an amount of at least 4 mole % and cholesterol in an amount of at least 10 mole %;
   wherein said first and second liposome have a mean diameter of 0.05 to 0.2 microns, whereby the second liposome contacts the first liposome to trigger the release of the therapeutic agent.

2. The method of claim 1 wherein the first liposome bears a net positive charge.

3. The method of claim 1 wherein the first and second liposomes are fusogenic.

4. The method of claim 1 wherein the first and second liposomes are protected with a fusogenic PEG coating.

5. The method of claim 1 wherein the second liposome is loaded with a different therapeutic agent than the first liposome.

6. The method of claim 1 wherein the subject is human.

7. The method of claim 1 wherein the therapeutic agent is an antineoplastic agent, an immunomodulating agent, a neuroactive agent, an antiflammatory agent, an antilipidemic agent, a hormone, a receptor agonist or antagonist, or an antiinfective agent.

8. A method according to claim 1 wherein the trigger is administered after the first liposome is administered.

9. A method according to claim 1 wherein the trigger is administered at a time to maintain a desired blood level of the therapeutic agent.

10. A method according to claim 1 wherein the trigger is administered at a predetermined interval after the first liposome is administered.

11. The method of claim 1 wherein the second liposome is loaded with the therapeutic agent.

12. The method of claim 1 wherein the first liposome comprises cholesterol, DOPE, distearoylphosphatidylcholine (DSPC) and the cationic lipid N,N-dioleyl-N,N-dimethylammonium chloride (DODAC), and the second liposome comprises cholesterol, DOPE, DSPC, and the anionic lipid dioleoyphosphatidylglycerol.

13. The method of claim 1 wherein the first liposome comprises cholesterol, DOPE, DSPC, and the anionic lipid dioleoyphosphatidylglycerol, and the second liposome comprises cholesterol, DOPE, distearoylphosphatidylcholine (DSPC) and the cationic lipid N,N-dioleyl-N,N-dimethylammonium chloride (DODAC).

14. The method of claim 1 wherein the therapeutic agent is doxorubicin.

* * * * *